United States Patent [19]

Eaton

[11] Patent Number: 5,428,149
[45] Date of Patent: Jun. 27, 1995

[54] METHOD FOR PALLADIUM CATALYZED CARBON-CARBON COULPING AND PRODUCTS

[75] Inventor: Bruce Eaton, Pullman, Wash.

[73] Assignee: Washington State University Research Foundation, Pullman, Wash.

[21] Appl. No.: 76,735

[22] Filed: Jun. 14, 1993

[51] Int. Cl.$^6$ .......................................... C07H 19/00
[52] U.S. Cl. ........................... 536/28.55; 536/28.1; 536/28.4; 536/28.5; 536/28.51; 536/28.52; 536/28.53; 536/28.54
[58] Field of Search .................... 536/28.1, 28.5, 28.53, 536/28.55, 28.52, 28.4, 28.54

[56] References Cited

U.S. PATENT DOCUMENTS

| Re. 34,069 | 9/1992 | Koster et al. | 536/25.3 |
|---|---|---|---|
| 4,415,732 | 11/1983 | Caruthers et al. | 536/26.5 |
| 4,725,677 | 2/1988 | Koster | 536/25.34 |
| 4,904,582 | 2/1990 | Tullis | 536/24.1 |
| 4,923,901 | 5/1990 | Koester et al. | 536/25.3 |
| 4,948,882 | 8/1990 | Ruth | 536/25.32 |
| 5,023,243 | 6/1991 | Tullis | 536/24.5 |
| 5,047,519 | 9/1991 | Hobbs, Jr. et al. | 536/28.5 |
| 5,118,672 | 6/1992 | Schinazi et al. | 514/47 |
| 5,118,800 | 6/1992 | Smith et al. | 536/23.1 |
| 5,118,802 | 6/1992 | Smith et al. | 536/25.3 |
| 5,134,066 | 7/1992 | Rogers et al. | 536/24.3 |
| 5,138,045 | 8/1992 | Cook et al. | 536/24.5 |

OTHER PUBLICATIONS

Crisp and Flynn (1990) Tetrahedron Letters 31:1347 "Palladium-catalyzed coupling of uridine triflate with organostannanes".
Yamamoto et al (1989) J. Org. Chem. 54:4734 "New method for the synthesis of boron-10 containing nucleoside . . . ".
Crisp (1989) Synthetic Communications 19:2117 "Synthesis of 5-alkenyl-2'-deosyuridines via organostannenes."
Bigge and Mertes (1981) J. Org. Chem. 46:1994 "A palladiuum-catalyzed coupling reaction and a photolytic . . . ".
Hacksell and Daves (1983) J. Org. Chem. 48:2870 "Stereo-controlled palladium (II)-mediated coupling of furanoid . . . ".
Gergstrom and Ruth (1976) J. Am. Chem. Soc. 98:1587 "Synthesis of C-5 sustituted pyrimidine nucleosides via organopalladium . . . ".
Bergstrom et al. (1982) J. Org. Chem. 47:2174 "Pyrido (2,3-d) pyrimidine nucleoside antibiotic . . . ".
Ruth and Bergstrom (1978) J. Org. Chem. 43:2870 "C-5 substituted pyrimidine nucleosides . . . ".
Bergstrom et al. (1981) J. Org. Chem. 46:1423 "Pyrrolo (2,3-d) pyrimidine nucleoside antibiotic analogues."
Bergstrom et al. (1981) J. Org. Chem. 46:1432 "C-5-- substituted pyrimidine nucleosides."
Stille (1986) Angew. Chem. Int. Ed. Engl. 25:508, "The palladium-catalyzed cross-coupling . . . ".
Arai and Daves (1970) J. Am. Chem. Soc. 100:287 "Regiospecific reaction of enol, ethers . . . ".
Still and Groh (1987) J. Am. Chem. Soc. 109:813 "Stereo-specific cross-coupling of vinyl halides . . . ".
Scott and Stille (1986) J. Am. Chem. Soc. 108:3033 "Palladium-catalyzed and coupling of vinyl triflates . . . ".
Paillargeon and Stille (1983) J. Am. Chem. Soc. 105:7175 "Direct conversion of organic halides to aldehydes . . . ".
Dreyer and Dervan (1985) Proc. Natl. Acad. Sci. USA 82:968 "Sequence-specific cleavage of single-stranded DNA . . . ".
Brown and Cooley (1990) Organometallics 9:353 "Mapping the reaction pathway in palladium-catalyzed . . . ".
Graaf et al. (1990) Organometallics 9:1479 "Cross-coupling versus homocoupling . . . ".
Albano and Castellari (1990) Organometallics 9:1269 "Synthesis and characterization of five-coordinate olefin . . . ".
Chemical Abstract: vol. 115: 92415h, Sentemov et al.

Primary Examiner—Douglas W. Robinson
Assistant Examiner—James Oliver Wilson
Attorney, Agent, or Firm—Swanson & Bratschun

[57] ABSTRACT

This invention discloses an improved method for the preparation of a superior palladim catalyst that is capable of coupling vinyl and aryl stannanes to 2'-deoxy-5-iodouridine.

9 Claims, 7 Drawing Sheets

R = 2',3',5'-tracetylribose

METHOD FOR PALLADIUM CATALYZED CARBON-CARBON COULPING AND PRODUCTS

FIELD OF THE INVENTION

This invention relates to the field of nucleic acid chemistry, specifically to a novel process for preparing 5-position modified pyrimidines, and an improved palladium catalyst capable of coupling modifying groups at the 5-position of pyrimidines. The present invention also includes the modified pyrimidines produced, and the methods of preparing the palladium catalyst.

BACKGROUND OF THE INVENTION

Until quite recently, the consideration of oligonucleotides in any function other than strictly informational was unheard of. Despite the fact that certain oligonucleotides were known to have interesting structural possibilities (e.g., t-RNAs) and other oligonucleotides were bound specifically by polypeptides in nature, very little attention had been focussed on the non-informational capacities of oligonucleotides. For this reason, among others, little consideration had been given to using oligonucleotides as pharmaceutical compounds.

There are currently at least three areas of exploration that have led to serious studies regarding the use of oligonucleotides as pharmaceuticals. In the most advanced of the fields, antisense oligonucleotides are utilized to bind to certain coding regions in an organism to prevent the expression of proteins or to block various cell functions. The discovery of RNA species with catalytic functions—ribozymes—has led to the consideration of RNA species that serve to perform intracellular reactions that will achieve desired effects. And lastly, the discovery of the SELEX process (Systematic Evolution of Ligands by Exponential Enrichment) has shown the research community that oligonucleotides can be identified that will bind to almost any biologically interesting target.

The use of antisense oligonucleotides as a method for controlling gene expression and the potential for using oligonucleotides as pharmaceutical materials has prompted investigations into the introduction of a number of chemical modifications into oligonucleotides to increase their therapeutic activity. Such modifications are designed to increase cell penetration of the oligonucleotides, to stabilize them from nucleases and other enzymes that degrade or interfere with the structure or activity of the oligonucleotide analogs in the body, to enhance their binding to targeted RNA, to provide a mode of disruption (terminating event) once sequence-specifically bound to targeted RNA, and to improve their pharmacokinetic properties. For example, PCT Patent Application Publication WO 91/14696, entitled: Oligonucleotide-Transport Agent Disulfide Conjugates, describes a method for chemically modifying antisense oligonucleotides to enhance entry into a cell.

A variety of methods have been used to render oligonucleotides resistant to degradation by exonucleases. PCT Patent Application Publication WO 90/15065, entitled: Exonuclease-Resistant Oligonucleotides and Methods for Preparing the Same, describes a method for making exonuclease-resistant oligonucleotides by incorporating two or more phosphoramidite and phosphoromonothionate and/or phosphorodithionate linkages at the 5' and/or 3' ends of the oligonucleotide. PCT Patent Application Publication WO 91/06629, entitled: Oligonucleotide Analogs with Novel Linkages, describes oligonucleotide compounds with one or more phosphodiester linkages between adjacent nucleotides replaced by a formacetal/ketal type linkage which are capable of binding RNA or DNA.

A common strategy for stabilization of RNA against endonucleolytic cleavage is to modify the 2'-position of ribonucleotides. One approach to stabilization against base-specific endonucleolytic cleavage rests on the interference with base recognition by enzymes. Several strategies for this modification are known, including modification with 2'-amino and 2'-fluoro (Hobbs et al. (1973) Biochemistry 12:5138; Guschlbauer et al. (1977) Nucleic Acids Res. 4:1933), and 2'-OCH$_3$ (Shibahara et al. (1987) 15:4403; Sproat et al. (1989) Nucleic Acids Res. 17:3373). PCT Patent Application Publication WO 91/06556, entitled: 2' Modified Oligonucleotides, describes nuclease-resistant oligomers with substituents at the 2' position. PCT Patent Application Publication WO 91/10671, entitled: Compositions and Methods for Detecting and Modulating RNA Activity and Gene Expression, describes antisense oligonucleotides chemically modified at the 2' position and containing a reactive portion capable of catalyzing, alkylating, or otherwise effecting the cleavage of RNA, a targeting portion, and a tether portion for connecting the targeting and reactive portions.

The 5-position of pyrimidines may also be chemically modified. The introduction of modifications at the C-5 position of pyrimidines may be envisioned to interfere with the recognition by pyrimidine specific endonucleases. However, this concept is not as clear cut as the modification of the 2'-position of ribonucleotides. The current understanding of the substrate recognition of pyrimidine specific nucleases, based on X-ray studies, postulates that O4 and N3 of the pyrimidines serve as hydrogen bond contact points (FIG. 1) (Takenaka et al. (1984) Nucleic Acids Symp. Ser. 15:113). Even the modified purine 8-oxo-guanosine-2'-monophosphate, which can provide these two contacts, serves as a tight binding inhibitor (Borkahoti and Palmer (1983) J. Mol. Biol. *169:743*).

Recent research has shown that RNA secondary and tertiary structures have important biological functions (Tinoco et al. (1987) Cold Spring Harb. Symp. Quant. Biol. 52:135; Larson et al. (1987) Mo. Cell. Biochem. 74:5; Tuerk et al. (1988) Proc. Natl. Acad. Sci. USA 85:1364; Resnekov et al. (1989) J. Biol. Chem. 264:9953). PCT Patent Application Publication WO 91/14436, entitled: Reagents and Methods for Modulating Gene Expression Through RNA Mimicry, describes oligonucleotide or oligonucleotide analogs which mimic a portion of RNA able to interact with one or more proteins. The oligonucleotides contain modified internucleoside linkages rendering them nuclease-resistant, have enhanced ability to penetrate cells, and are capable of binding target oligonucleotide sequences.

Palladium-catalyzed reactions involving organotin compounds have been explored for many years. These reactions constitute some of the best ways to form new carbon-carbon bonds. The reactions are generally characterized as substitution or addition reactions between an organotin species and an organic electrophile.

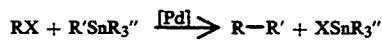

When the electrophile is an acyl halide, or similar species, carbonylation substitution occurs as follows:

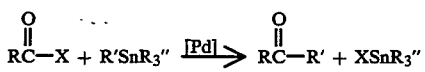

Carbonylative substitution may also be accomplished using an alkyl halide, carbon monoxide and an organotin species in the presence of a palladium catalyst.

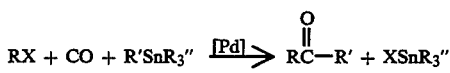

Early reviews of palladium-catalyzed substitution and addition reactions by Stille and Mitchell provide a great deal of information regarding the scope of the reaction and variations that are acceptable and desirable in certain situations. See, Stille (1986) Angew. Chem. 98:504; Angew. Chem. Inst. Ed. Engl. (1986) 25:508; Mitchell (1986) J. Organomet. Chem. 304:1. A more recent review of palladium-catalyzed reactions of organotin compounds is also available. See, Mitchell (1992) Angew. Chem. Int. Ed. Engl. 9:803–815.

Although there has been a great deal of effort in studying the palladium-catalyzed reactions, extension of the system to new reactions is not always straightforward. As stated recently by Professor Mitchell when reviewing the recent literature, "particular attention will be paid to catalyst variations, since the choice of the right catalyst for a particular task often appears from the literature to involve a fair degree of alchemy", Mitchell supra.

The use of palladium to catalyze carbon-carbon bond formation at the 5 position of pyrimidine nucleosides is not unknown. The first use of this technique was demonstrated by Bergstrom (Bergstrom et al. (1976) J. Am. Chem. Soc. 98:1587, (1978) J. Org. Chem. 43:2870, (1981) J. Org. Chem. 46:1432 and 2870, (1982) J. Org. Chem. 47:2174) and Daves (Arai and Daves (1978) J. Am. Chem. Soc., 100:287; Lee and Daves (1983) J. Org. Chem. 48:2870). Bergstrom and Daves used 5-mercurialdeoxyuridine compounds, the same as those used by Dreyer and Dervan ((1985) Proc. Natl. Acad. Sci. USA 82:968) to tether functional groups to oligonucleotides.

One method for simple carbon-carbon coupling reactions to the 5-position of uridines is described in the work of Crisp (1989) Syn. Commun. 19:2117. Crisp forms deoxyuridines functionalized at the 5 position by reacting protected 5-iodo-2'-deoxyuridine with alkenyl-stannanes in acetonitrile in the presence of a Pd (II) catalyst. Crisp's protocol differs from that of the present invention in three important ways. First, it requires acetonitrile as solvent and uses PdCl$_2$(PPh$_3$)$_2$ as catalyst. This catalyst does not work well when THF is used as the solvent. Second, the Crisp catalyst has less general applicability, being incapable of facilitating the coupling of aromatic groups. Thirdly, the prior art methods required protection/deprotection schemes. Further, independent attempts to repeat literature procedures involving Pd(II) species have shown that the results were not reproducible. In a later paper [(1990) Tetrahedron Lett. 31:1347] Crisp used the 5-triflate uridines to react with the organostannanes, to synthesize 5-aryl and 5-vinyl uridine analogs. The 5-triflate uridine starting materials are very difficult to prepare.

SELEX (Systematic Evolution of Ligands for Exponential Enrichment) is a method for identifying and producing nucleic acid ligands, termed "nucleic acid antibodies", e.g., nucleic acids that selectively bind to target molecules (Tuerk and Gold (1990) Science 249:505). The method involves selection from a mixture of candidates and step-wise iterations of structural improvement, using the same general selection theme, to achieve virtually any desired criterion of binding affinity and selectivity. Starting from a mixture of nucleic acids, the method includes steps of contacting the mixture with the target under conditions favorable for binding, partitioning unbound nucleic acids from those nucleic acids which have bound to target molecules, dissociating the nucleic acid-target pairs, amplifying the nucleic acids dissociated from the nucleic acid-target pairs to yield a ligand-enriched mixture of nucleic acids, then reiterating the steps of binding, partitioning, dissociating and amplifying through as many cycles as desired.

The methods of the present invention may be combined with SELEX to produce nucleic acid antibodies containing modified nucleotides. The presence of modified nucleotides may result in nucleic acid antibodies with an altered structure exhibiting increased capacity to bind target molecules. The steric and electronic influence of 5-position modified nucleotides may also act to prevent nuclease degradation.

BRIEF SUMMARY OF THE INVENTION

The present invention includes a novel method for introducing functional groups, including carbonyl, alkenyl or aryl groups at the 5-position of the pyrimidine ring utilizing a novel palladium catalyst.

Included in the present invention is a method for the preparation of a significantly more active palladium catalyst for carbon-carbon bond formation that achieves improved yields of vinyl and aryl coupling products. The novel catalyst so produced is also included as part of this invention.

This invention includes a reaction scheme for producing a wide variety of 5-position modified pyrimidine molecules. The key element in the production of the 5 modified pyrimidines is the use of a novel palladium catalyst. The improved PL$_3$ catalysts of the present invention act to accelerate the formation of products that could be formed only slowly and in low yields utilizing the catalysts of the prior art.

Novel compounds that can be prepared according to the methods of this invention include the 5 position modified uridines of the general formula:

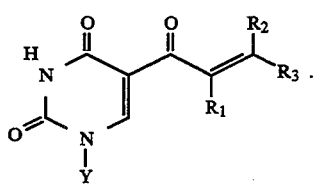

The present invention further includes the production of cytidine analogs.

This invention further includes a method of preparing stabilized nucleic acids wherein a substitution at the 5-position is coupled to a substitution in the 2-position.

DETAILED DESCRIPTION OF THE INVENTION

Figure 1:
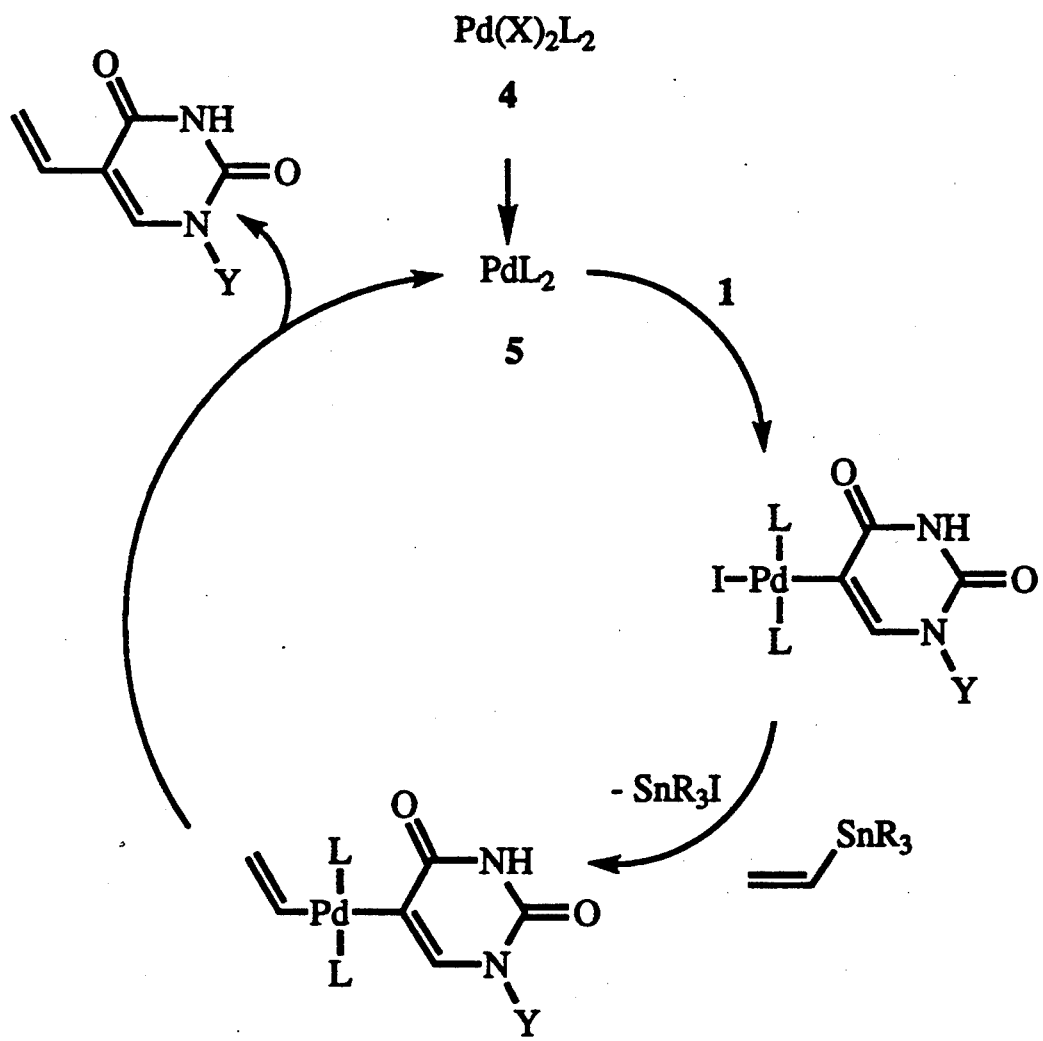
FIG. 1 shows the prior art mechanism first proposed by Stille of palladium catalyzed coupling of alkenylstannanes to alkenyltriflates, adapted to uridine chemistry.

The present invention includes a method for introducing carbonyl, alkenyl or aryl groups at the 5-position of the pyrimidine ring via a palladium catalyst. In one embodiment of the invention, a novel palladium catalyst is utilized to affect the cross-coupling of 5-halouridines or 2'-deoxy-5-halouridines and a variety of organostannanes.

Included in the present invention is a method for the preparation of a significantly more active palladium catalyst for carbon-carbon bond formation that achieves improved yields of vinyl and aryl coupling products, including products predicted by the prior art not to be formable. The novel catalyst so produced is also included as part of this invention, Illustrative pyrimidine analogs produced by the method of the present invention are shown in Table 1. Group A molecules are the result of palladium catalyzed carbonylative C—C coupling and Group B molecules are prepared by simple C—C coupling. The present invention further includes the production of cytidine analogs.

TABLE I

| | Group A | Group B |
|---|---|---|
| (structure shown) | 1 R' = CHO | 8 R' = C$_6$H$_5$ |
| | 2 R' = COCHCH$_2$ | 9 R' = CHCH$_2$ |
| | 3 R' = COE—CHCHCH$_3$ | 10 R' = E—CHCHCH$_3$ |
| | 4 R' = COE—CHCHSi(CH$_3$)$_3$ | 11 R' = E—CHCHSi(CH$_3$)$_3$ |
| | 5 R' = COC(OC$_2$H$_5$)CH2 | 12 R' = C(OC$_2$H$_5$)CH$_2$ |
| | 6 R' = COE—CHCHCHO | 13 R' = E—CHCHCHO |
| | 7 R' = COC$_6$H$_5$ | |
| | R = ribose | |

Table 1 represents only a partial list of the 5 position uridine substitutions that can be produced according to the methods of the present invention. Of the compounds listed in Table 1, the inventors hereto believe that compounds 2, 3, 4, 5, 6, 7, 12 and 13 are novel compounds.

One class of 5-substituted pyrimidines that are novel to this invention are depicted as follows:

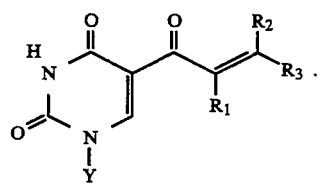

R$_1$, R$_2$ and R$_3$ may be hydrogen, or an alkyl, alkenyl, alkynyl, alkoxy, halo or phenyl group or any other stable substituent that may commonly be attached to an unsaturated carbonation. This novel class of materials is particularly well suited for forming additional compounds of interest by acting as a Michael adduct acceptor. Y may be any ribose, deoxy ribose or any substituent commonly attached to this position of the uridine ring. This class of compounds cannot be prepared in acceptable yields according to prior art methods.

A second class of 5-substituted pyrimidines that are novel to this invention are depicted as follows:

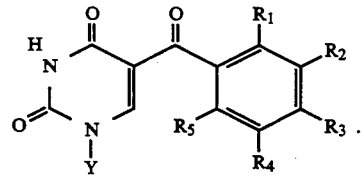

R$_1$, R$_2$, R$_3$, R$_4$ and R$_5$ may be hydrogen, or an alkyl, alkenyl, alkynyl, alkoxyl, phenyl, halo, cyano group or any other stable substituent that may commonly be attached to an aromatic ring.

The present invention extends to all such novel compounds that can be prepared according to the methods of the present invention. The present invention also includes oligonucleotides that contain one or more of the novel C-5 substituted uridines of this invention.

This invention includes a reaction scheme for producing 5-position modified pyrimidine molecules. The key element in the production of the 5 modified pyrimidines is the use of a novel palladium catalyst. Although palladium catalyzed C—C and C—CO coupling reactions have been known for some time, a possibly erroneous proposed mechanism for the reaction has led others away from recognizing that a PL$_3$ type catalyst would provide a more effective catalytic species that would allow for the formation of some 5-pyrimidine analogs previously unattainable with the use of known palladium coupling catalysts. In general, the palladium catalyzed organostannane coupling reactions have utilized PL$_4$ catalysts. The improved PL$_3$ catalysts of the present invention act to accelerate the formation of products that could be formed only slowly and in low yields or not at all utilizing the catalysts of the prior art.

The catalyst of the present invention may be characterized most generally as PdL₃, where L is one of any number of commonly employed ligands of palladium. It is within the skill and knowledge of those skilled in the art to recognize the various ligands that may be employed. In the preferred embodiments of the catalytic species of this invention L=PPh₃ (triphenyl phosphine, or P(C₆H₅)₃). Pd(PPh₃)₃ is a coordinantly unsaturated species, and although not limited by theory, may exist as a dimer in solution. In THF, it is likely that in solution the palladium in PdL₃ is solvent coordinated to fill the vacancy of the metal center (18 electrons, or Pd(O) tertacoordinate).

The preparation of the preferred catalyst of the present invention is described in Example 1. In the preferred embodiment the improved catalyst composition of the present invention is comprised of a solution of Pd(OAc)₂ and P(C₆H₅)₃, wherein the molar ratio of P(C₆H₅)₃ to PD(OAc)₂ is about 3. In the preferred embodiment the catalyst composition also includes CuI.

According to the present invention, the novel carbon-carbon coupling catalyst of the general structure PdL₃ is a more reactive catalyst useful for any palladium catalyzed organostannane coupling or addition reaction.

The general reaction of the present invention can be characterized as follows:

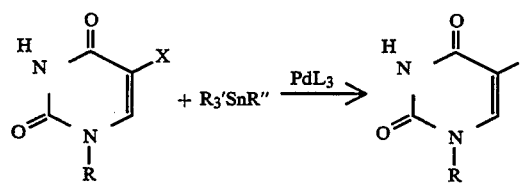

R' can be selected from a wide variety of functional groups, as is shown in Table I. Group A compounds in Table I are the result of carbonylative C—C coupling, while Group B molecules are prepared by simple C—C coupling. More specifically, R' may be any R group with a bond or atom capable of coordination to palladium and allowing for transmetallation. The bond must be connected directly to the tin or no further removed than one saturated carbon.

In the preferred embodiments of the method of this invention, the PdL₃ catalyst is prepared in THF solvent, and the reaction is run in the THF solvent. Other acceptable solvents include acetonitrile, dioxane, acetone, tetrahydropyran and morpholine.

In the most general embodiments of this invention, X is any of a number of acceptable leaving groups well known to those skilled in the art, including acetate, trifluoroacetate, trifluoromethyl sulfonate and boronic esters and acids. In the preferred embodiment, X is a halogen, and in the most preferred embodiment X is iodine.

The catalyst and solvent system of the present invention is 6–10 times faster (at 60° C.) than prior art systems, depending on the type of group being coupled.

The 5 modified uridines of the present invention are contemplated for use in oligonucleotides that act as ligands to biological targets. Stability towards endonucleolytic degradation in serum can be achieved by introducing 2'-deoxy-2'-fluoro- or 2'-deoxy-2'-aminonucleosides to the pyrimidine positions of the ligand (Pieken et al. (1991) Science 253:314). The 5 position modified pyrimidines of the present invention may also be coupled with 2' substituted species that would also be useful in a variety of situations.

Groups A and B of Table I could be further divided into three categories whose effect on RNA ligands could strengthen binding: molecules 9–12 and their hydrogenated derivatives could serve to enhance the hydrophobic interactions of ligands to their targets; molecules 1–8, 14, and 15 could all form reversible imine crosslinks with amino groups of peptides or proteins. In addition, favorable interactions may occur with polysaccharides by the formation of hemiacetal linkages to these groups; and molecules 2–6 and 14 could undergo Michael addition with amines or thiols. The crosslinking groups may be most important for improving the stability of secondary and higher order oligonucleotide structure.

Example I below provides a comparison of a variety of palladium catalysts in performing the coupling of a number of species at the 5 position of pyrimidine.

It is believed that an erroneous mechanism for palladium catalyzed reactions has led away from the use of PdL₃ species.

TABLE II

EFFECT OF METHOD OF CATALYST PREPARATION ON PRODUCT YIELD

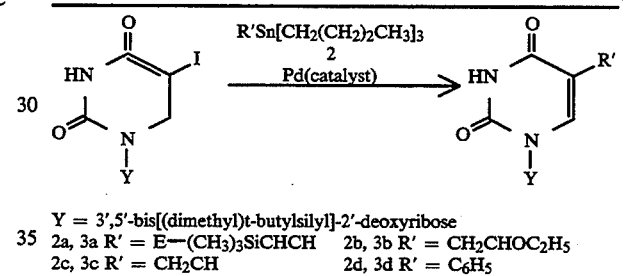

Y = 3',5'-bis[(dimethyl)t-butylsilyl]-2'-deoxyribose
2a, 3a R' = E—(CH₃)₃SiCHCH  2b, 3b R' = CH₂CHOC₂H₅
2c, 3c R' = CH₂CH          2d, 3d R' = C₆H₅

| Reaction | Catalyst | Time (h) | % Yield |
|---|---|---|---|
| 2a + 1 | A | 1.25 | 71 |
| | B | 1.25 | 0 |
| | C | 1.25 | 43 |
| | A | 1.50 | 86 |
| | D | 36.0 | 5 |
| 2b + 1 | A | 36.0 | 82 |
| | D | 192.0 | 70 |
| 2c + 1 | A | 14.0 | 72 |
| | D | 120.0 | 0 |
| 2d + 1 | A | 36.0 | 76 |
| | D | 144.0 | 0 |

Catalyst compositions. Catalyst A is comprised of 10 mol % Pd(OAc)₂, 30 mol % P(C₆H₅)₃, and 30 mole % CuI. Catalyst B is comprised of 10 mol % Pd(OAc)₂, 40 mol % P(C₆H₅)₃, and 30 mol % CuI. Catalyst C is comprised of 10 mol % Pd₂[(C₆H₅CHCH)₂CO]₃ and 60 mole % P(C₆H₅)₃. Catalyst D is comprised of Pd[P(C₆H₅)₃]₄.

Because the initial catalytic step in all the reactions shown in Table 2 involve oxidative addition of Pd(0) to a carbon-iodide bond, it is necessary to invoke some initial redox chemistry that converts at least a portion of Pd(II) to Pd(0). The mechanism first proposed by Stille in relation to palladium catalyzed coupling of alkenylstannanes to alkenyltriflates (Scott and Stille (1986) J. Am. Chem. Soc. 108:3033) was adapted to the chemistry discussed here as shown in FIG. 1.

It is uncertain whether the redox process 4–5 shown in FIG. 1 occurs. However, oxidative addition of Pd(II) to a carbon-X bond (where X is I or triflate) to give a Pd(IV) species is significantly exothermic (deGraff et al. (1990) Organometallics 9:1479) and only in special circumstances are these complexes not decomposed, thereby casting doubt on the importance of high oxidation state palladium in the catalytic cycle.

It was noted by the present inventors that the major difference between typical Pd(0) and Pd(II) coupling reactions was subsequent to the redox step and concerned whether two or four phosphine ligands were available to bind to the metal. To the best of the inventors knowledge, no prior example of $PdL_3$ (where L is triphenylphosphine) catalyzed carbon-carbon coupling has been reported. It was reasoned that three phosphine ligands should give a superior catalyst compared to $PdL_4$ which is coordinatively saturated and $PdL_2$ a 14 e complex that would prefer to form metal clusters. The formation of $PdL_3$ (catalyst A, Table 2) in THF provides good yields and faster reaction to form the coupling products shown in Table 2. In contrast to all methods previously reported for palladium catalyzed coupling of alkenyl or aryliodides to tin substrates, phenyltributyl and alkenyltributylstannanes were both used successfully, employing the same catalyst in THF.

This is the first report of a palladium catalyst that couples ethoxyethenetributylstannane (2b) to 1 to give the new nucleotide analog 3b.

Previous reports on alkenylstannane couplings to 2'-deoxyuridine have postulated that electron withdrawing groups attached to the alkene carbon and decreased steric bulk at tin accelerated the rate of reaction. In some cases it was necessary to substitute trimethylaryl- for tributylarylstannanes (Stille and Groh (1987) J. Am. Chem. Soc. (1987) supra). In light of these observations 2b with its electron donating ethoxy group and sterically demanding tributyl substituents would appear to be unsuitable for this reaction.

Figure 2:
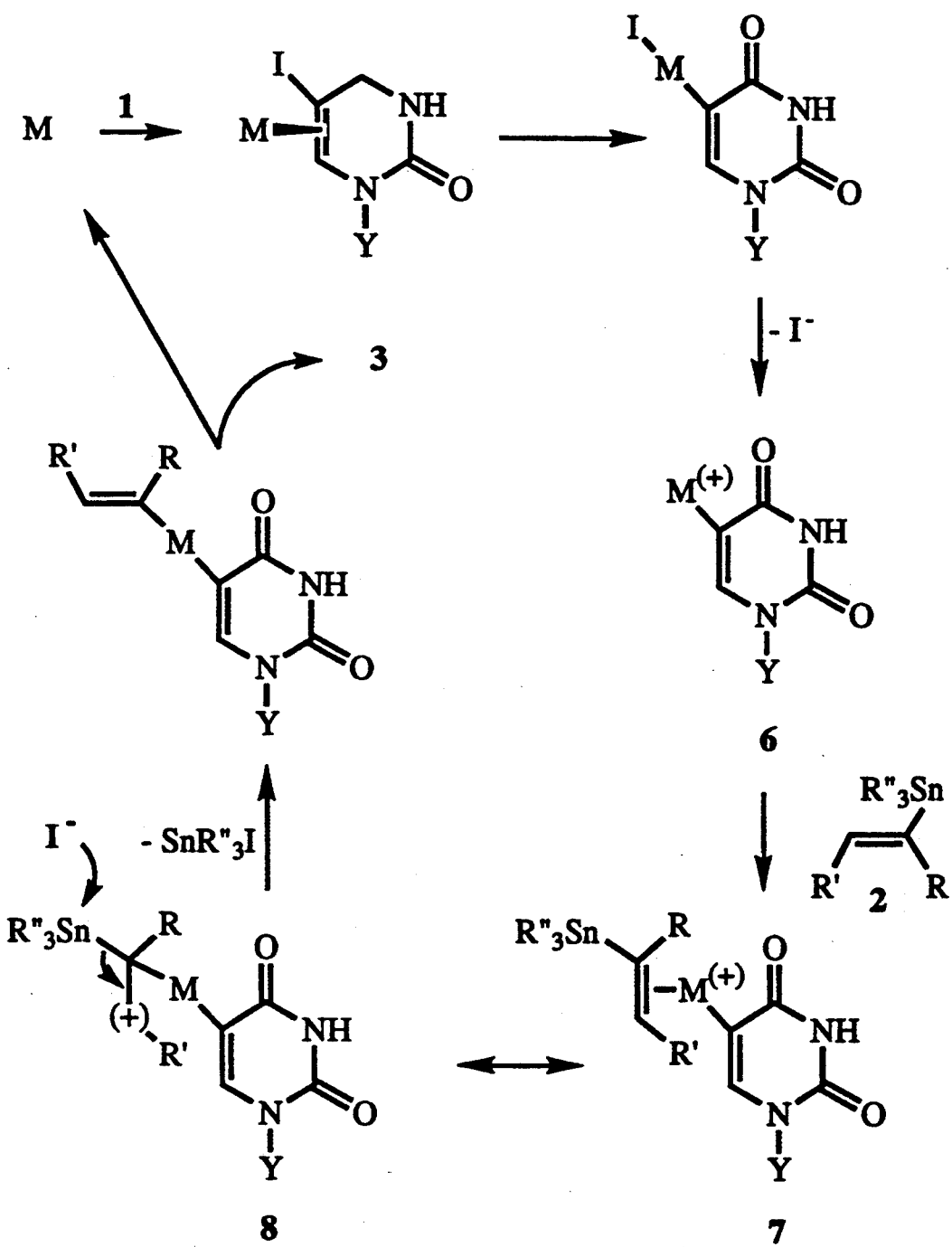
FIG. 2 shows the proposed mechanism for palladium catalyzed iodouridine to stannane cross-coupling.

To explain the discrepancy between earlier reports on palladium catalyzed iodouridine to stannane cross-coupling and the results disclose herein an alternative mechanism is proposed (FIG. 2).

The major differences between the schemes depicted in FIGS. 1 and 2 are that in the latter phosphine ligands are not required to be displaced by relatively weak $\pi$-ligands (the alkenyl- and arylstannanes) and that the formation of the cationic complex 6 is facilitated by the coordination of three phosphines (Albano et al. (1990) Organometallics 9:1269). The first step in the mechanism of FIG. 2 involves coordination of the alkene with subsequent oxidative addition into the C-I bond. These details are not shown in FIG. 2 but have been experimentally verified (Brown and Cooley (1990) Organo-Metallics 9:353). It should be noted that when four phosphine ligands per metal are present, phosphine could compete with the tin substrate as a ligand in going from 6 to 7. This may explain the relatively slow or undetectable rate for those entries in Table 3 regarding catalyst D and the lower yield of catalyst E.

Cation 7 has a resonance contributor 8, suggesting that some positive charge would be on the $\beta$-carbon to the tin. The magnitude of the charge borne by the $\beta$-carbon would be dictated by the substituents R and R' and therefore could influence the rate of catalysis. (Collman et al. (1987) *Principles and Applications of Organotransition Metal Chemistry*, University Science Books, Mill Valley, Calif.).

Other explanations are possible for the increased activity of the $PdL_3$ catalyst A. It was important to determine if the copper complexes formed in the preparation of A improved the catalytic activity. To test this possibility, $PdL_3$ was synthesized by an expensive alternative route devoid of copper (catalyst C). Tris(dibenzylidene-acetone)dipalladium 9 was treated with 6 equivalents of triphenylphosphine in THF at room temperature. Within seconds of adding the triphenyl phosphine the distinctive red color of 9 was replaced by the gold color characteristic of $PdL_3$. Table 3 shows that this catalyst C was similar in reactivity to that formed using Cu(I) reduction of Pd(II) (catalyst A). The prior art use of palladium and tin compounds to react with uridines uses cumbersome protection steps that are not compatible with subsequent chemistry and must be removed. The method of the present invention eliminates the need for many of these steps.

According to one embodiment of this invention, carbonylative coupling can be performed with nucleosides only protected at the 5'-OH with DMT. The modified DMT-nucleoside products are ready for preparation of the phosphoramidate and subsequent automated oligonucleotide synthesis. Examples of such reactions are as follows:

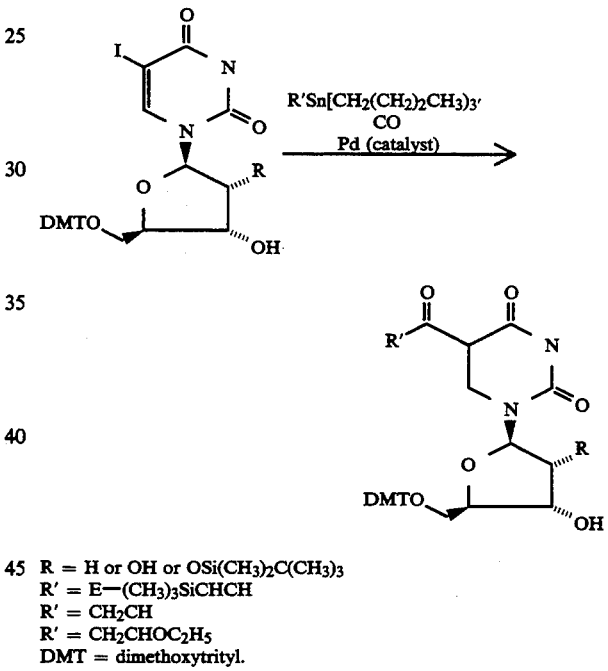

R = H or OH or $OSi(CH_3)_2C(CH_3)_3$
R' = E—$(CH_3)_3SiCHCH$
R' = $CH_2CH$
R' = $CH_2CHOC_2H_5$
DMT = dimethoxytrityl.

The ability to perform these reactions on the unprotected nucleoside is important because protection/deprotection schemes are expensive and counterproductive. An experimental protocol is given in Example 4 below.

The coupling chemistry of this invention works equally as well for the ribose derivatives. To the best of the knowledge of the inventors hereto, no catalytic palladium chemistry for the modification of ribose nucleosides has been reported. For many applications it is necessary to turn the modified nucleosides into triphosphates. The method of the present invention works even when the 5'-OH is not protected, as shown below. This is a surprising result because carbonylative ester formation is known to occur if hydroxyl groups are present. Apparently, the rate of product formation is faster than competing reactions to form esters when using $PdL_3$ for this catalyst preparation.

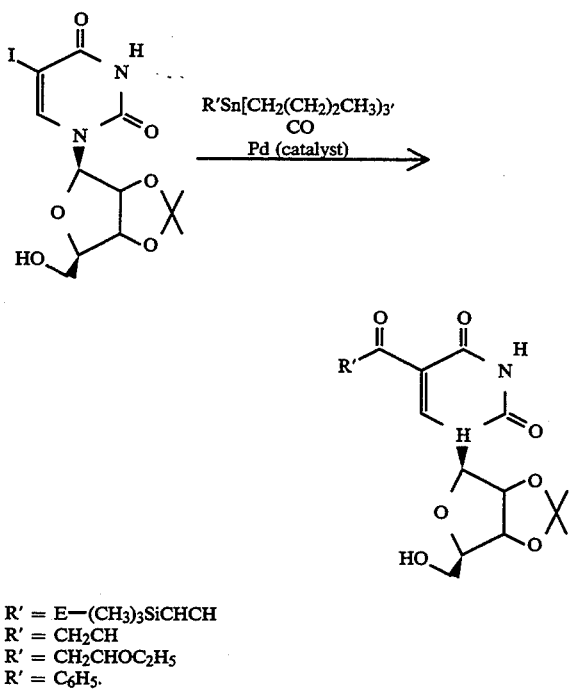

R' = E—(CH3)3SiCHCH
R' = CH2CH
R' = CH2CHOC2H5
R' = C6H5.

For solubility reasons, and because it is required for the triphosphate synthesis, the 5-iodouridine is protected as the acetonide. Again, the modified nucleoside is ready for the next step without deprotection. An example of the synthetic procedure is given in Example 5 below.

Figure 6:
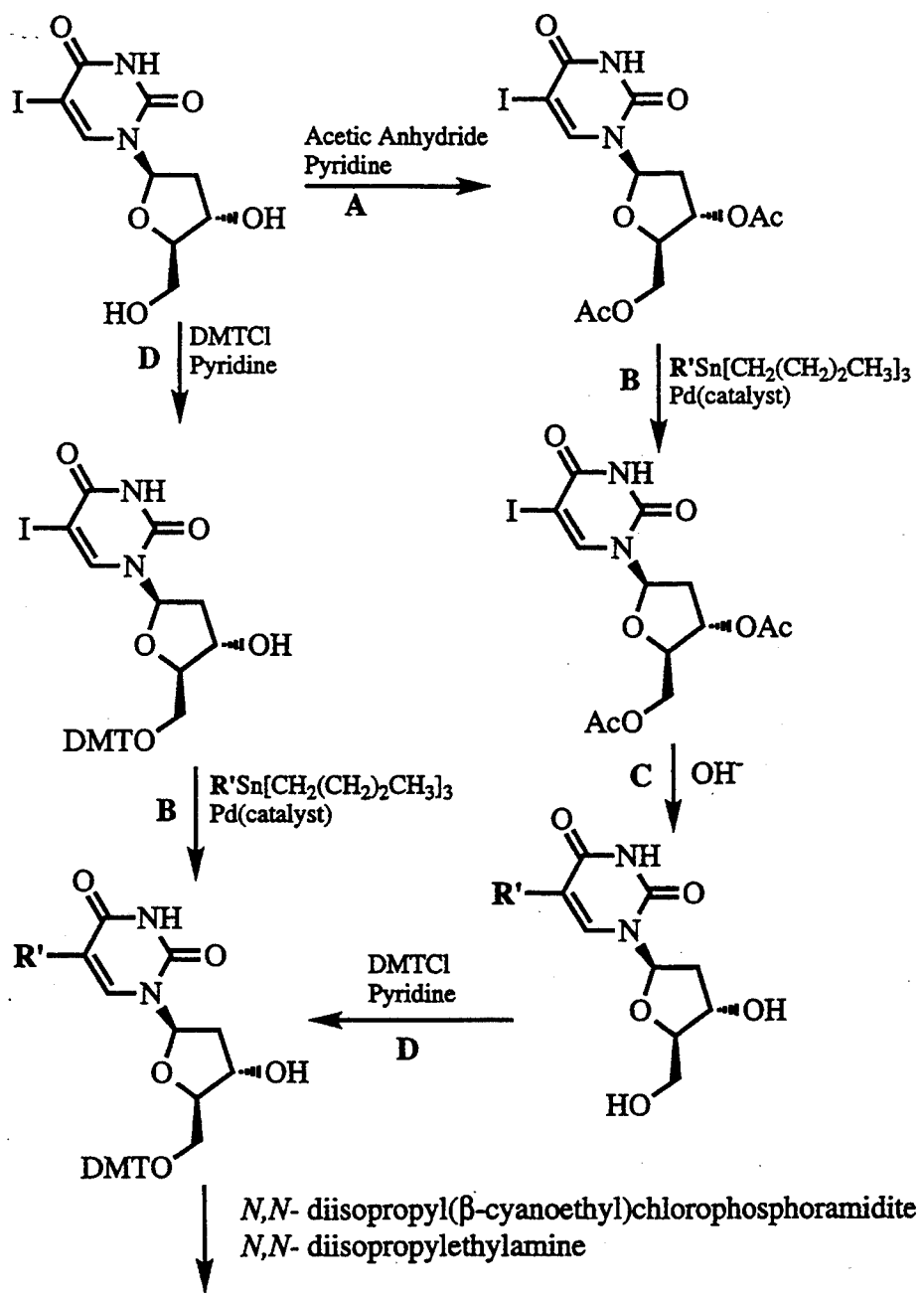
FIG. 6 depicts two reaction schemes for the production of C-5 substituted uridine reagents for use in automated DNA synthesis.
Figure 7:
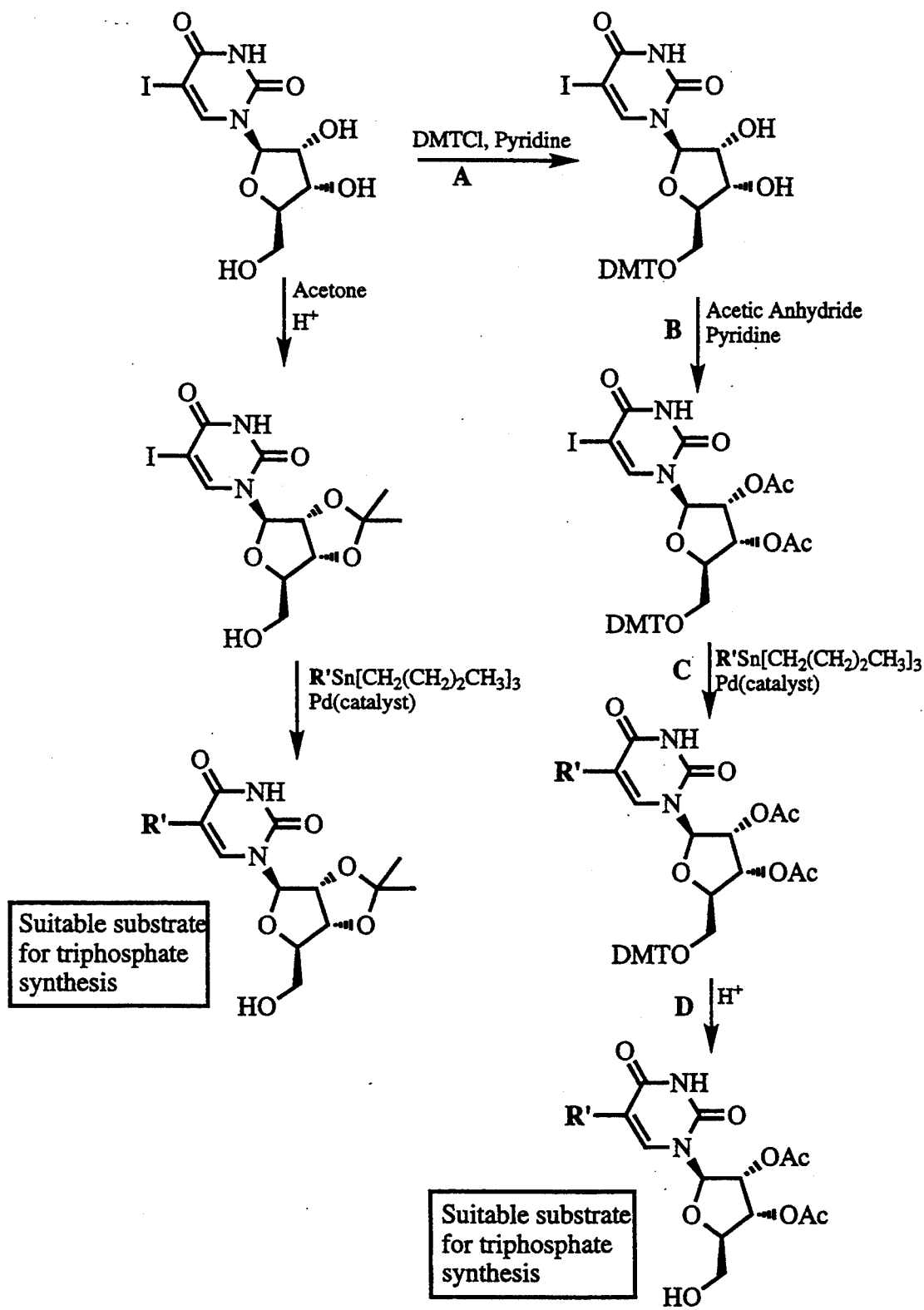
FIG. 7 depicts two reaction schemes for the production of C-5 substituted uridine reagents for use in automated RNA synthesis.

In FIGS. 6 and 7, reaction schemes are depicted that dramatize the importance of the present invention. In particular, the ability to perform the coupling reactions without certain protection/deprotection steps saves considerable effort in the preparation of reagents for use in the automated synthesis of oligonucleotides.

Referring to FIG. 6, the goal is to produce the C-5 substituted deoxyribose protected at the 5'-OH with DMT. This material is then converted into the phosphoramidate, which is the principle reagent for automated DNA synthesis. If prior art palladium catalyzed coupling reactions are used, it would be necessary to follow the reaction pathway A, B, C and D. Utilizing the novel method of the present invention, only steps D and B are required to yield the desired product.

FIG. 7 illustrates the same savings in steps for the production of reagents useful for the automated synthesis of ribonucleotide triphosphates. In this case, following reaction pathway A, B, C and D yields 2', 3' protected C-5 substituted uridine. The present invention teaches, however, that only steps E and F are necessary to yield a suitable RNA synthesis reagent due to the fact that the 5' OH does not need to be protected using the present method.

Figure 5:
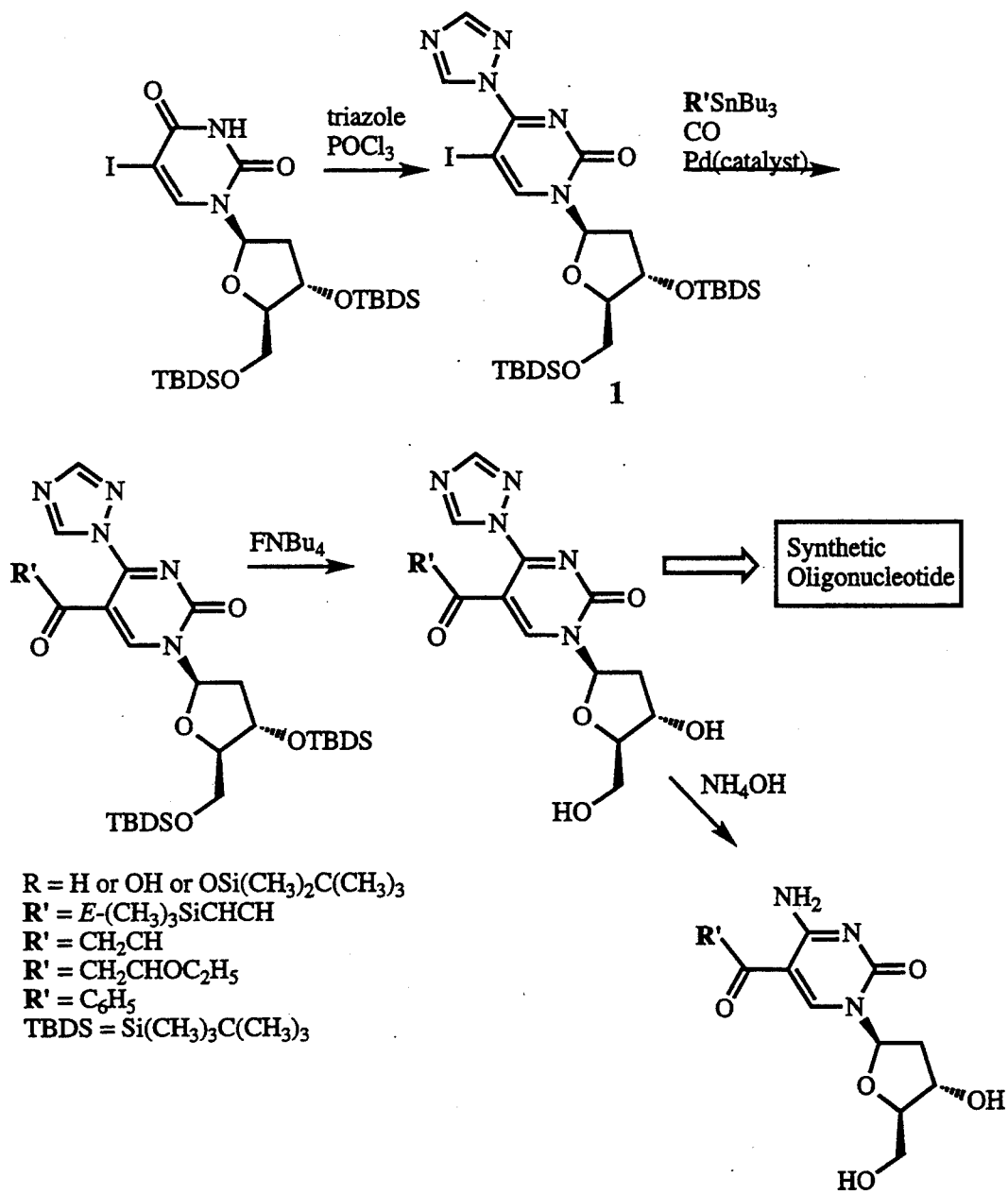
FIG. 5 shows a reaction scheme for the preparation of modified cytidines.

The preparation of modified cytidine and 2'-deoxycytidine is also possible according to the present invention. FIG. 5 depicts a reaction scheme for the synthesis of modified cytidines.

It will be noted that for automated oligonucleotide synthesis that the triazole may be converted directly into the phosphoramidate and used to prepare synthetic oligonucleotides. This has been done in RNA (Sung (1982) J. Org. Chem. 47:3623). On standard deprotection subsequent to oligonucleotide synthesis, aminolysis converts the triazole to the exocyclic 4-amino group of cytidine. The synthesis of the catalyst coupling substrate (1 in FIG. 5) is described in Example 6 below.

One objective in the chemical modification of ligands is the formation of more compact structures to reduce the overall size of the ligand. One strategy towards this goal is the introduction of moieties into the RNA that will allow additional stabilizing interactions. The formation of additional salt bridges within an RNA oligonucleotide will greatly enhance its repertoire of possible structures. One of the most studied and best understood salt bridge formation between RNA and proteins is that of arginine to the phosphodiester backbone (Tao and Frankel (1992) Proc. Natl. Acad. Sci. USA 89:2723). Frankel and coworkers have established that a single arginine can bind tightly to a specific structural motif on tar RNA by specific hydrogen bonding (Puglisi et al. (1992) Science 257:76). Thus, a pyrimidine analog carrying an arginine side chain at the C-5 position may increase the repertoire of RNA structures and thus RNA ligands.

C-5-(2-arginyl-ethylketo)-uridine was prepared by the method of the present invention which allows the facile synthesis of the 5-(2-ene1-one)-uridine. This precursor can act as a Michael acceptor for the addition of arginine.

The arginyl side chain also enhances the possibility of evolving RNA ligands to acidic proteins, which generally are not disposed to interact with polyanionic oligonucleotides.

One other amino acid functionality that is particularly attractive is the cysteinyl side chain, which may allow formation of intramolecular disulfide bridges within the RNA ligand. It furthermore may participate in disulfide exchanges with the target. This may be exploited for high affinity binding to such disulfide rich peptides as vasopressin. In this case, disulfide exchange with existing disulfide bridges within the peptide after binding of the ligand may proceed in quasi intramolecular fashion. Since the reaction is reversible it fulfills the criterion of high selectivity and consequently should dramatically reduce the off-rate of the ligand.

The incorporation of C-5 halogenated nucleosides may also prove valuable for enhanced ligand-target interaction. The commercially available 5-bromouridine for instance, once incorporated into an oligoribonucleotide is activated for slow nucleophilic attack at the C-6 position. Other electron withdrawing groups at the C-5 position may also serve this purpose.

Methods have been described that allow the functionalization of the C-6 position of pyrimidines (Chemistry of Nucleosides and Nucleotides (Townsend ed.), 1988 Plenum Publishing Corp., New York; pp. 39). The latter serves as precursor for the introduction of a carboxylate, methyl, carboxymethyl, or halomethyl group. A carboxylate at this position may serve as a precursor for further condensations with, for example, alkyl amine spacers. Thus a whole range of groups can also be attached at the C-6 position, which can be coupled with the C-5 modified molecules of the present invention.

There is a whole range of reporter groups that can be incorporated into RNA by automated RNA synthesis. Phosphoramidite building blocks for the incorporation of the most common reporter functionalities, such as the fluorescent fluorescein group or biotin, are commercially available. Generic amino-linker building blocks with a variety of linker arm sizes are also available, so that other fluorescent dyes such as rhodamine can be easily introduced.

A highly sensitive detection system ideally is designed in such a way that the fluorescence is not turned on until an actual ligand-target interaction occurs. This concept has been realized with DNA hybridization probes with intercalating cyanine dyes (Rye et al. (1992) Nucleic Acids Res. 20:2803).

A biotin-based detection system may also be used. A series of commercially available biotinylated monomers may be added to a given RNA ligand by automated solid phase synthesis, binding to avidine, which has a reporter enzyme bound to it, typically HRP. Turn over of the reporter enzyme with a suitable substrate will then generate signal, typically chemiluminescence.

The method of the present invention may be used to produce cytidine analogs. It has been determined that the triazole group of 4-position will not react with the palladium catalyst or tin reagent of the present invention even under more drastic conditions than required for C—C coupling to occur.

Figure 3:
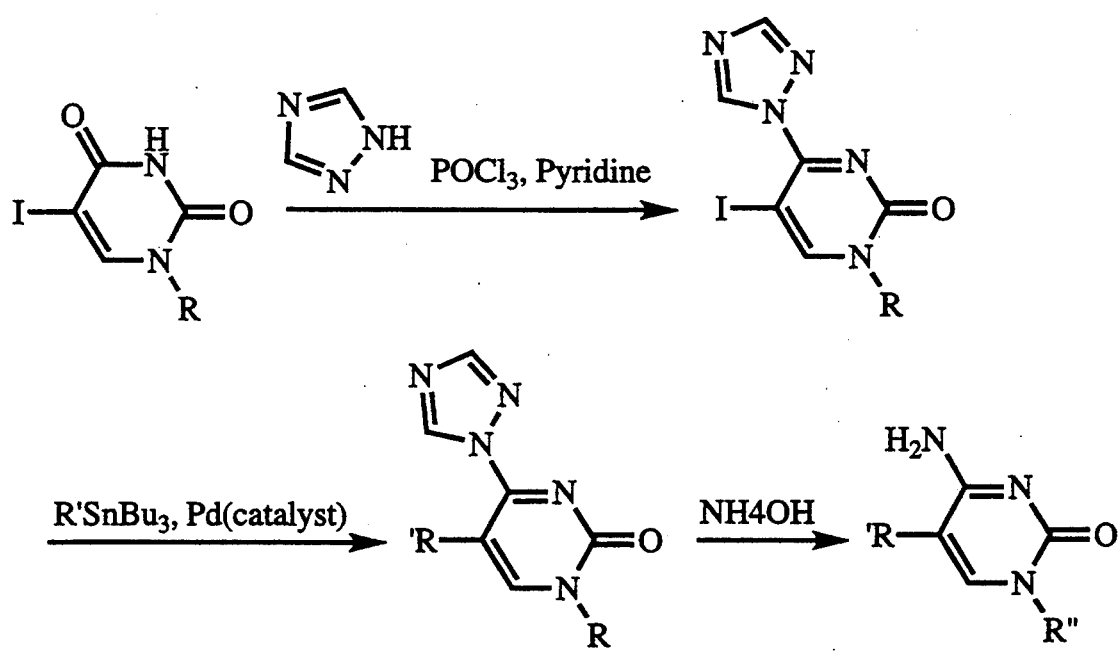
FIG. 3 shows a reaction scheme for synthesizing uridine and cytidine derivities.

FIG. 3 shows one approach for utilizing the same catalytic palladium coupling chemistry to accomplish the synthesis of both uridine and cytidine derivatives. However, transformation of thymidine to cytidine subsequent to attachment of groups to the 5-position is also possible, although in some cases this strategy may require protecting groups.

Figure 4:
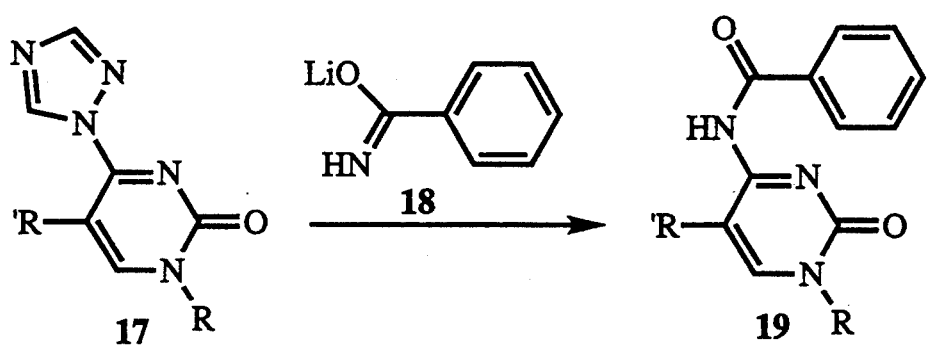
FIG. 4 shows an alternate mechanism for synethsizing cytidine derivitives.

Another approach to the synthesis of protected cytidine derivatives is shown in FIG. 4. The reaction of the amidate ion 18 with the triazole nucleosides 17 may provide the N⁴-benzoylcytidines 19 in one step. For the synthesis of phosphoramidites and triphosphates this would be an attractive alternative.

It is anticipated that standard protecting groups will suffice for the preparation of 5-position modified cytidine phosphoramidites. Synthesis of the triphosphates will be performed as described by Eckstein (1989) supra. Standard methods will be used in the preparation of phosphoramidites, but may require the implementation of protecting groups to avoid side reactions with 5-position substituents that contain carbonyls that can form enols.

To compliment the 5-position modified pyrimidine oligonucleotides of the present invention, it is useful to test the inclusion of modified bases in RNA ligands. Both simple C—C and carbonylative C—C coupling reactions may be prepared at the 8-position of purines using catalytic palladium chemistry. The 8-bromo adenine and guanine nucleosides are suitable starting material and are commercially available.

In addition to the functional groups shown in Table I, it may be desirable to incorporate other functional groups, such as amino, thiol, and carboxy, at the 5-position. This is best achieved by linkage of a nucleoside via a Michael addition. It has been shown that amino acids undergo clean reaction with the product of FIG. 8 to form a number of carboxy substituted (amino acids) 2'-deoxyuridines. This chemistry may be expanded to include uridines. In addition, it may be possible to perform the Michael reaction subsequent to the incorporation of these modified bases into oligonucleotides. If true this would mean that only one Michael acceptor functionality would need to be accommodated by T7 polymerase.

Example 1. Catalyst Composition and Preparation and Comparision With Existing Catalyst Systems Independent attempts to repeat literature procedures involving Pd(II) species have shown that results were not reproducible. Experiments performed with either $PdCl_2L_2$ or $Pd(OAc)_2L_2$ species, where $L_2$ is $2P(C_6H_5)_3$, $2P(o-CH_3C_6H_4)_3$, or $[(C_6H_5)_2PCH_2]_2$, under argon using rigorously purified solvents gave only traces of the expected product or no reaction. Similarly, tetrakis-(triphenylphosphine)palladium (catalyst D of Table II) was found to reproducibly couple only two of the substrates tested.

The reaction scheme used to test the effectiveness of various palladium catalysts was the 5-position reaction of 2'-deoxy-5 iodouridine as shown below:

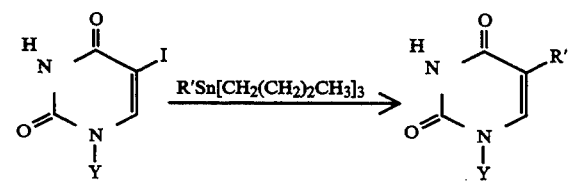

$Y = 3'$-$5'$-bis [(dimethyl)t-butylsilyl]-2'-deoxyribose
2a, 3a R' = E—$(CH_3)_3$SiCHCH     2b, 3B R' = $CH_2CHOC_2H_5$
2c, 3c R' = $CH_2CH$     2d, 3d R' = $C_6H_5$.

Example 2. Preparation of 3a

The following reagents were combined in a glass reaction vessel equipped with a Teflon vacuum stopcock in a Vacuum Atmospheres Inc. inert atmosphere (argon) glove box: 1 (0.400 mmol), $Pd(OAc)_2$ (0.04 mmol), CuI (0.12 mmol), $P(C_6H_5)_3$ (0.12 mmol), THF (10 ml, distilled from benzophenone Na/K alloy) and 2a (0.48 mmol). After stirring for 90 minutes at 70° C., the solvent was removed by rotary evaporator. The resulting brown oil was dissolved in methylenechloride (4 ml) and applied to a pad of silica (9 g) in a glass-fritted Buchner funnel (30 ml). The silica was eluted with additional methylenechloride (30 ml). The methylenechloride eluent was discarded and the product eluted with diethyl ether (80 ml). The ether solution was concentrated on a rotary evaporator and the resulting residue purified by flash chromatography (40 g $SiO_2$, 20% ethylacetate in hexanes) to give 3a (191 mg, 86%).

Characterization of Product 3a. Melting point 206.0°-206.6° C.; UV(THF)$\lambda_{max}$(log $\epsilon$) 248(4.12), 296(4.04); IR ($CH_2Cl_2$) 2956, 2931, 2958, 1711, 1691, 1622, 1462, 1362, 1278, 1251 cm$^{-1}$; $^1$H NMR (200 MHz, $CDCl_3$) $\delta$7.97 (bs, 1H), 7.64 (s, 1H), 6.67 (d, J=19 Hz, 1H), 6.54 (d, J=19 Hz, 1H), 6.28 (dd, J=8, 6 Hz, 1H), 4.40 (dt, J=6, 2 Hz, 1H), 3.96 (q, J=2 Hz, 1H), 3.85 (dd, J=11, 2 Hz, 1H), 3.75 (dd, J=11, 2 Hz, 1H), 2.29 (ddd, J=13, 6, 2 Hz, 1H), 2.00 (ddd, J=13, 8, 6 Hz, 1H), 0.89 (s, 9H), 0.88 (s, 9H), 0.09 (s, 9H), 0.08 (s, 3H), 0.07 (s, 3H), 0.06 (s, 3H), 0.05 (s, 3H); $^{13}$C NMR (125 MHz, $CDCl_3$) $\delta$162.0, 149.5, 136.5, 134.6, 131.6, 113.8, 88.2, 85.6, 72.5, 62.3, 41.7, 25.9, 25.7, 18.4, 18.0, −1.3, −4.7, −4.9, −5.2, −5.5; MS (70 eV) m/z 554 (M+, 10), 69 (100), 149 (50), 213 (10), 256 (20), 368 (22), 410 (10); HRMS (70 eV) m/z 554.3019 ($M^+$, calcd 554.3018).

Characteristics of Product 3b. MP 139.5°-140.1° C.; UV(THF)$\lambda_{max}$(log $\epsilon$) 234(3.99), 292(4.03); IR ($CH_2Cl_2$) 3378, 2955, 2931, 2858, 2360, 2341, 1714, 1692, 1630, 1464, 1304 cm$^{-1}$; $^1$H NMR (200 MHz, $CDCl_3$) $\delta$8.46 (bs, 1H), 7.86 (s, 1H), 6.25 (dd, J=7, 6 Hz, 1H), 5.34 (d, J=2 Hz, 1H), 4.39 (dt, J=6, 2 Hz, 1H), 4.34 (d, J=2Hz, 1H), 3.95 (dt, J=6, 2 Hz, 1H), 3.83 (q, J=7 Hz, 2H), 3.75 (dd, J=12, 2Hz, 1H), 3.65 (dd, J=12, 2 Hz, 1H), 2.34 (ddd, J=13, 6, 2 Hz, 1H), 2.02 (ddd, J=13, 8, 6 Hz, 1H), 1.33 (t, J=7 Hz, 3H), 0.88 (s, 9H), 0.86 (s, 9H), 0.07 (s, 6H), 0.04 (s, 3H), 0.03 (s, 3H); $^{13}$C NMR (125 MHz, CDCl$_3$) δ160.6, 151.3, 149.3, 137.0, 110.0, 88.0, 87.1, 85.9, 72.4, 63.0, 62.5, 40.7, 25.8, 25.7, 18.3, 18.0, 14.5, −4.8, −4.9, −5.5, −5.6; MS (70 eV) m/z 526 (M+, 10) 59 (36), 73 (100), 88 (59), 115 (15), 145 (52), 149 (28), 182 (12), 257 (10), 287 (15), 337 (23); HRMS (70 eV) m/z 526.2897 (M+, calcd 526.2894).

Characteristics of product 3c. $^1$H NMR (200 MHz, CDCl$_3$) d 8.55 (bs, 1H), 7.65 (s, 1H), 6.34 (dd, J=18, 11 Hz, 1H), 6.29 (dd, J=8, 6 Hz, 1H), 5.98 (dd, J+18, 2 Hz, 1H), 5.22 (dd, J=11, 2Hz, 1H), 4.38 (dt, J=6, 2 Hz, 1H), 3.95 (q, J=2, 1H), 3.82 (dd, J=12, 2 Hz, 1H), 3.72 (dd, J=112, 2 Hz, 1H), 2.29 (ddd, J=13, 6, 2 Hz, 1H), 1.99 J=13, 8, 6 Hz, 1H), 0.89 (s, 9H), 0.87 (s, 9H), 0.08 (s, 6H), 0.06 (s, 3H), 0.05 (s, 3H); $^{13}$C NMR (125 MHz, CDCl$_3$) δ161.8, 149.4, 136.6, 128.0, 116.3, 112.6, 88.1, 85.4, 72.3, 63.0, 41.6, 25.9, 25.7, 18.4, −1.3, −4.7, −4.9, −5.4, −5.5. Desilytated 3c gave 2'-deoxy-5-etheneuridine with physical properties of those reported previously (Jones et al.)

Characteristics of product 3d. $^1$H NMR (200 MHz, CDCl$_3$) δ8.89 (bs, 1H), 7.76 (s, 1H), 7.45 (m, 2H), 7.32 (m,3H), 6.36 (dd, J=8, 6 Hz, 1H), 4.38 (dt, J+6, 2 Hz, 1H), 3.96 (q, J=3 Hz, 1H), 3.82 (dd, J=12, 2 Hz, 1H), 3.72 (dd, J+12, 2 Hz, 1H), 2.32 (ddd, J-13, 6, 2 Hz, 1H), 2.03 (ddd, J=13, 8, 6 Hz, 1H), 0.88 (s, 9H), 0.73 (s, 9H), 0.07 (s, 3H), 0.05 (s, 3H), −0.05 (s, 3H), −0.012 (s, 3H); $^{13}$C NMR (125 MHz, CDCl$_3$) δ162.2, 150.0, 137,0, 132.5, 128.5, 128.4, 127.9, 115.6, 88.1, 85.5, 72.4, 63.0, 41.5, 25.7, 25.6, 18.2, 17.9, −4.7, −4.9, −5.70. Desilytated 3d gave 2'-deoxy-5-phenyluridine with physical properties of those reported previously (Bigge et al. (1981) J. Org. Chem. 46:1994).

Example 3. 5-position modified rimidines 5-benzophenone and 5-ethylsilane modified uridine and cytidine were synthesized by the methods of the present invention and converted to the triphosphates by the method of Ludwig and Eckstein (1989) J. Org. Chem. 54:631. These triphosphates may be tested as substrates for T7 RNA polymerase. The modified oligoribonucleotides were tested as templates for reverse transcriptase. The fidelity of the two enzymes with 5-modified substrates/template was also tested.

Example 4. Reaction of Uridine Unprotected Other Than at the 5'-OH Position

One example of nucleoside carbonylative insertion starting with 5-iodo-5'-dimethoxytrityl-2'-deoxyuridine is given by the synthesis of 5-formyl-5'-dimethoxytrityl-2'-deoxyuridine. The following reagents were combined in the reaction flask portion of a self-contained glass coupling apparatus equipped with a pressure equalizing addition funnel and Teflon valves in a Vacuum Atmospheres, Inc., inert atmosphere (argon) glove box: 5-iodo-5'-dimethoxytrityl-2'-deoxyuridine (0.400 mmol), Pd(OAc)$_2$, (0.04 mmol), CuI (0.12 mmol), P(C$_6$H$_5$)$_3$ (0.12 mmol) and THF (20 mL, distilled from benzophenone Na/K alloy). Tributyltinhydride (0.440 mmol in 10 Ml of THF) was added to the addition funnel portion of the coupling apparatus. The reaction apparatus was charged with 50 psi of CO and heated to 55° C. Tributyltinhydride was dispensed using the addition funnel at a rate of 70 to 100 μl/min. After 8 hours at 55° C. the solvent was removed on a rotary evaporator. The crude product was dissolved in dichloromethane (3 mL) and applied to a pad of silica (18 g) in a glass-fritted Büchner funnel (60 mL). The silica was eluted with pentane (50 mL) followed by dichloromethane (50 mL). The pentane/CH$_2$Cl$_2$ eluent was discarded and the product eluted with ethyl acetate (100 mL). The ethyl acetate solution was concentrated on a rotary evaporator and the resulting residue purified by flash chromatography (80 g SiO$_2$ 230–400 mesh; 10% CH$_3$OH/CH$_2$—Cl) to give 5-formyl-5'-dimethoxytrityl-2'-deoxyuridine (150 mg, 84%).

Example 5. Modification of 5-iodo-5'-acetyl-3,2'-isopropylidineuridine

A typical procedure for nucleoside carbonylative insertion starting with 5-iodo-5'-acetyl-3'2'-isopropylidineuridine is given by the synthesis of 5-formyl-5'-acetyl-3'2'-isopropylidineuridine. The following reagents were combined in the reaction flask portion of a self-contained glass coupling apparatus equipped with a pressure equalizing addition funnel and Teflon valves: 5-iodo-5'-acetyl-3',2'-isopropylidineuridine (0.221 mmol), Pd(OAc)$_2$ (0.022 mmol), CuI (0.066 mmol), P(C$_6$H$_5$)$_3$ (0.066 mmol) and THF (20 mL, distilled from benzophenone Na/K alloy), Tributyltinhydride (0.243 mmol in 10 mL of THF) was added to the addition funnel portion of the coupling apparatus. The reaction apparatus was charged with 50 psi of CO and heated to 55° C. Tributyltinhydride was dispensed using the additional funnel at a rate of 70 to 100 μL/min. After 8 hours at 55° C. the solvent was removed on a rotary evaporator. The crude product was dissolved in CH$_2$Cl$_2$ (4 mL) and applied to a pad of silica (18 g) in a glass-fritted Büchner funnel (60 mL). The silica was eluted with pentane (50 mL) followed by a dichloromethane (50 mL). The pentane/dichloromethane eluent was discarded and the product eluted with ethyl acetate (100 mL). The ethyl acetate solution was concentrated on a rotary evaporator and the resulting residue purified by flash chromatography (80 g SiO$_2$ 230–400 mesh; 40% hexanes in ethyl acetate) to give 5-formyl-5'-acetyl-3'2'-isopropylidineuridine (59.8 mg, 80%).

Example 6. Synthesis of Modified Cytidine Substrates

The following reagents were combined in a 200-mL roundbottomed flask under argon: 1,2,4-Triazole (16.8 mmol), POCl$_3$ (3.82 mmol), N(O$_2$H$_5$)$_3$ (19.6 mmol) and CH$_3$CN (100 mL). The resulting solution was cooled to 0° C. and 5-iodo-3',2'-bis(t-butyldimethylsilyl)-2'-deoxyuridine (0.85 mmol) in CH$_3$CN (35 mL) was added drop-wise using a syringe. The reaction mixture was allowed to warm to room temperature over 6 hours. The CH$_3$CN solution was concentrated on a rotary evaporator and the resulting residue dissolved in ethyl acetate (70 mL). This solution was extracted 3 times with H$_2$O (100 mL) followed by brine (100 mL). The ethyl acetate layer was collected and dried using MgSO$_4$ (1 g). The ethyl acetate solution was concentrated on a rotary evaporator and the resulting oil dried invacuo (10$^{-3}$mmHg). Crystallization from ethyl acetate/hexanes gave I (496 mg 92%). Palladium catalysis was performed as discussed above.

I claim:

1. A method for the preparation of pyrimidine nucleosides modified at the 5-position of the pyrimidine ring from a pyrimidine starting material containing a halogen leaving group attached to the 5-position of the pyrimidine ring, such method comprising the steps of: preparing a solution of a palladium catalyst of the formula PdL$_3$, wherein L is triphenyl phosphine (PPhd$_3$);

reacting said pyrimidine starting material with a tetraalkyl tin compound of the formula R'SnR₃", wherein R" is selected from the group consisting of an alkyl of C1–C4 carbon and R' is selected from the group consisting of a carbonyl of C1–C7 C1–C7 carbons, a carbalkoxy of C1–C5 carbons, an alkenyl of C1–C3 carbons, an alkoxy of C1–C4 carbons or phenyl (C₆H₅), with the palladium catalyst; and isolating and purifying said modified pyrimidine nucleoside.

2. The method of claim 1 wherein said pyrimidine starting material is a 5-halo-uridine.

3. The method of claim 2 wherein said 5-halo-uridine is 5-iodo-uridine.

4. The method of claim 1 wherein the catalyst is comprised of Pd(OAc)₂ and P(C₆H₅)₃.

5. The method of claim 4 wherein the molar ratio of P(C₆H₅)₃ to Pd(OAc)₂ is about 3.

6. The method of claim 1 wherein R' is:

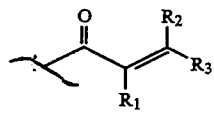

and wherein $R_1$, $R_2$ and $R_3$ are independently selected from the group consisting of: H, $CH_3$, $Si(CH_3)_3$, OR, CHO, phenyl, wherein R is selected from the group consisting of an alkyl of C1–C2 carbons.

7. The method of claim 4 wherein said catalyst further comprises CuI.

8. The method of claim 4 wherein said catalyst solution is prepared in a solvent selected from the group consisting of THF, acetonitrile, oxane, acetone, tetrahydropyran and morpholine.

9. The method of claim 7 wherein the molar ration of P(C₆H₅)₃, CuI and Pd(OAc)₂ is about 3:3:1.

* * * * *

UNITED STATES PATENT AND TRADEMARK OFFICE
CERTIFICATE OF CORRECTION

PATENT NO. : 5,428,149                                          Page 1 of 2
DATED     : JUNE 27, 1995
INVENTOR(S) : EATON It is certified that error appears in the above-indentified patent and that said Letters Patent is hereby corrected as shown below:

Fig. 3 (Sheet 3 of 7), the word "triacetylribose" is incorrectly spelled as "tracetylribose". Appearing directly below the word triacetylribose the designation for ribose is incorrectly indicated with a double prime. The "R" attached to N in the final structure in Figure 3 was incorrectly typed as an "R"."

Sheet 3, Fig. 3, the word "triacetylribose" is incorrectly spelled as "tracetylribose".

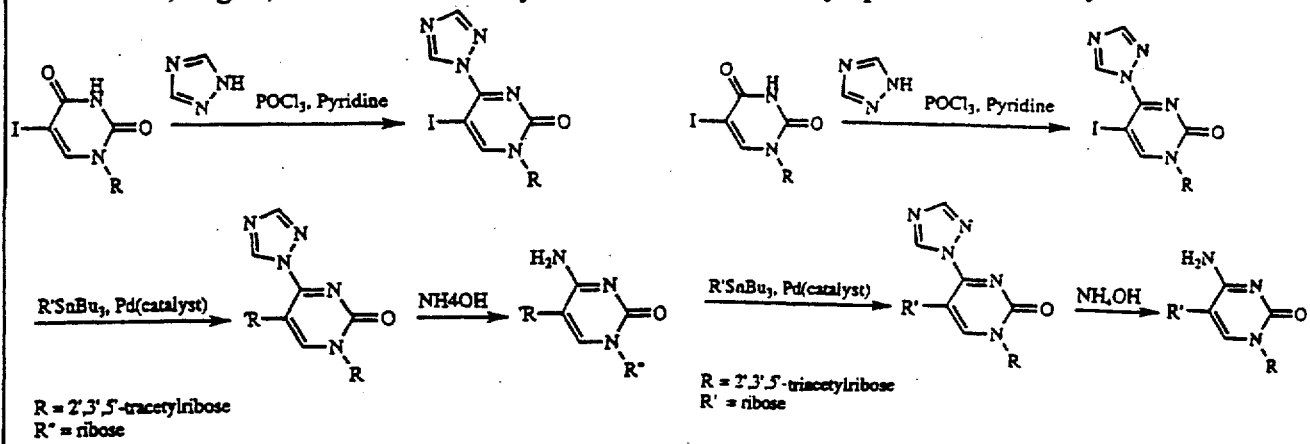

FIG. 3                                  FIG. 3

Incorrect                               Correct

UNITED STATES PATENT AND TRADEMARK OFFICE
CERTIFICATE OF CORRECTION

PATENT NO. : 5,428,149
DATED : JUNE 27, 1995
INVENTOR(S) : EATON

It is certified that error appears in the above-indentified patent and that said Letters Patent is hereby corrected as shown below:

Fig. 4 (Sheet 4 of 7), the word "triacetylribose" is incorrectly spelled as "tracetylribose".

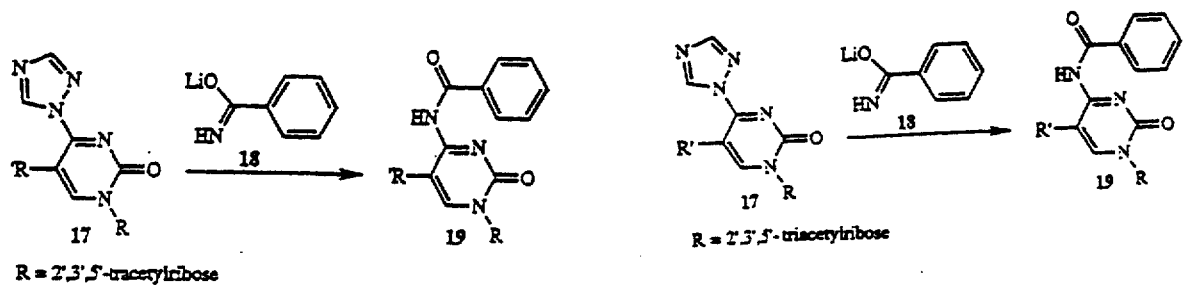

Incorrect            Correct

Signed and Sealed this

Fourteenth Day of July, 1998

Attest:

BRUCE LEHMAN

Attesting Officer     Commissioner of Patents and Trademarks